United States Patent [19]

Spivack et al.

[11] 4,093,618
[45] June 6, 1978

[54] AMIDES OF 2,4,6-TRIALKYL-3-HYDROXY-PHENYLALKANOIC ACIDS

[75] Inventors: John D. Spivack, Spring Valley; Martin Dexter, Briarcliff Manor, both of N.Y.

[73] Assignee: Ciba-Geigy Corporation, Ardsley, N.Y.

[21] Appl. No.: 693,387

[22] Filed: Jun. 7, 1976

Related U.S. Application Data

[60] Division of Ser. No. 494,156, Aug. 2, 1974, Pat. No. 3,988,363, which is a continuation-in-part of Ser. No. 400,603, Sep. 25, 1973, abandoned.

[51] Int. Cl.² .............................................. C07D 295/18
[52] U.S. Cl. .............................. 544/387; 260/45.8 N; 260/45.85 S; 260/559 R
[58] Field of Search ...................... 260/268 C

[56] References Cited

U.S. PATENT DOCUMENTS

| | | | |
|---|---|---|---|
| 3,763,176 | 10/1973 | Dexter et al. | 260/268 C |
| 3,984,460 | 10/1976 | Spivack | 260/268 |
| 3,988,363 | 10/1976 | Spivack et al. | 260/268 |

Primary Examiner—Nicholas S. Rizzo
Attorney, Agent, or Firm—Luther A. R. Hall

[57] ABSTRACT

Ester and amides having the formula

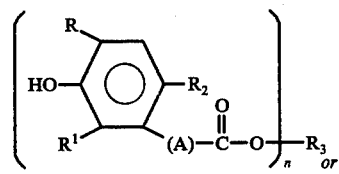

I

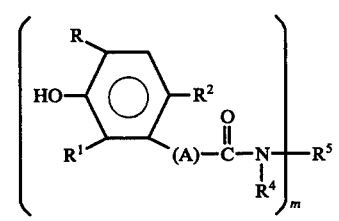

II wherein R, $R^1$ and $R^2$ are independently lower alkyl or cycloalkyl groups, $R^3$ is hydrogen, alkyl, cycloalkyl, alkylene, phenyl, phenyl substituted by alkyl groups, alkylthioethyl, thiobis-alkylene, alkyleneoxyalkylene, polyoxyalkylene or a polyvalent cyclic or acyclic hydrocarbon radical, $R^4$ is hydrogen, lower alkyl, cycloalkyl, $R^5$ is hydrogen, alkyl, phenyl, phenyl substituted by alkyl groups, alkylene, a polyvalent cyclic or acyclic hydrocarbon radical or alkyleneoxyalkylene, A is lower alkylene, $m$ is 1 to 4 and $n$ is 1 to 6.

4 Claims, No Drawings

AMIDES OF 2,4,6-TRIALKYL-3-HYDROXY-PHENYLALKANOIC ACIDS

This application is a divisional of copending application Ser. No. 494,156, filed Aug. 2, 1974, now U.S. Pat. No. 3,988,363, issued Oct. 26, 1976, which in turn is a continuation-in-part of application, Ser. No. 400,603, filed Sept. 25, 1973, now abandoned.

The esters are prepared by usual esterification procedures from a suitable alcohol and an acid of the formula III

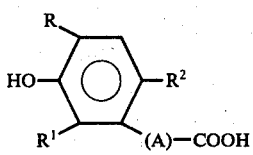

or an aicd halide or acid anhydride thereof. The higher alkyl esters can also be prepared from the lower alkyl ester, especially the methyl ester, by transesterification with a higher alkanol or polyol.

The amides are prepared by usual amidation procedures by reacting a carboxylic acid of formula III, an acid chloride, anhydride or a lower alkyl ester thereof with the appropriate amine.

The nitriles corresponding to acids of formula III are prepared as well as some malonate esters derived having the formula V.

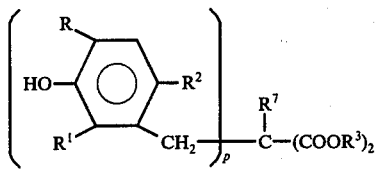

The compounds are useful as stabilizers of organic materials, especially polyolefins, which deteriorate upon exposure to light and heat.

DETAILED DISCLOSURE

This invention pertains to esters and amides of 2,4,6-trialkyl-3-hydroxyphenylalkanoic acids and to organic materials normally subject to oxidative, thermal and UV light deterioration stabilized with said ester and amide compounds. More specifically, the compounds of this invention are those having the formula I or II:

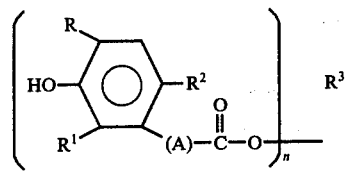

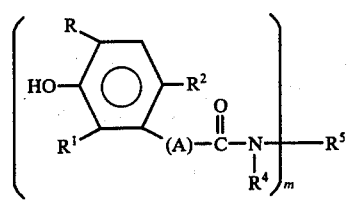

wherein
R, $R^1$ and $R^2$ are independently lower alkyl of 1 to 8 carbon atoms or a cycloalkyl of 5 to 6 carbon atoms, provided that there are no more than 2 cycloalkyl groups, $R^3$ is hydrogen, alkyl of 1 to 24 carbon atoms, cycloalkyl of 5 to 6 carbon atoms, phenyl, phenyl substituted with alkyl groups, said alkyl groups having 1 to 18 carbon atoms, alkylthioethyl of 4 to 27 atoms in the chain, thiobis-alkylene of 5 to 9 atoms in the chain, alkylene of 2 to 12 carbon atoms, cycloalkylene of 5 to 8 carbon atoms, alkylene of 7 to 10 carbon atoms containing a cycloalkane group in the chain, alkyleneoxyalkylene of 5 to 9 atoms in the chain, polyoxyalkylene of 8 to 101 atoms, or a polyvalent acyclic or cyclic hydrocarbon radical of 3 to 10 carbon atoms, $R^4$ is hydrogen, lower alkyl of 1 to 8 carbon atoms, cycloalkyl of 5 to 6 carbon atoms, $R^4$ and $R^5$ together form a piperazinyl ring incorporating both nitrogen atoms when $m$ is 2, or the group

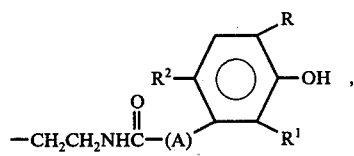

$R^5$ is hydrogen, alkyl of 1 to 24 carbon atoms, phenyl, phenyl substituted with alkyl groups, said alkyl groups having 1 to 18 carbon atoms, alkylene of 2 to 12 carbon atoms, a polyvalent cyclic or acyclic hydrocarbon radical of 3 to 8 carbon atoms or alkyleneoxyalkylene of 5 to 9 atoms in the chain, A is a straight or branched lower alkylene having 1 to 8 carbon atoms or a 1,1-alkylidene of 2 to 8 carbon atoms, $m$ is an integer of 1 to 4, and $n$ is an integer of 1 to 6.

The R, $R^1$ and $R^2$ groups can be straight or branched lower alkyl groups having 1 to 8 carbon atoms as, for example, methyl, ethyl, propyl, butyl, amyl, heptyl or octyl. R, $R^1$ and $R^2$ can be cycloalkyl of 5 to 6 carbon atoms such as cyclopentyl or cyclohexyl. Preferably R is a branched alkyl group of 3 to 8 carbon atoms such as isopropyl, sec-butyl, tert-butyl, sec- and tert-amyl, sec- and tert-hexyl, sec- and tert-heptyl or sec- and tert-octyl, and most preferably a tert-butyl group. $R^1$ and $R^2$ are preferably an alkyl group having 1 to 3 carbon atoms such as methyl, ethyl or n-propyl and most preferably the methyl group.

The $R^3$ group can be alkyl of 1 to 24 carbon atoms such as methyl, n-butyl, n-octyl, n-dodecyl, n-octadecyl or n-tetracosanyl. Preferably $R^3$ is an alkyl group of 1 to 18 carbon atoms such as n-dodecyl or n-octadecyl.

The $R^3$ group also is cycloalkyl of 5 to 6 carbon atoms, preferably cyclohexyl.

$R^3$ is also phenyl or phenyl substituted with alkyl groups, said alkyl groups having 1 to 18 carbon atoms. The substituents may be methyl, isopropyl, tert-butyl and tert-octyl. Substitution in the ortho or para positions of the phenyl ring is especially preferred. Preferably $R^3$ is phenyl substituted with alkyl groups having 1 to 12 carbon atoms and most preferably 1 to 8 carbon atoms such as two tert-butyl groups.

$R^3$ can also be alkylthioethyl of 4 to 27 atoms in the chain and having the general structure $-CH_2CH_2SR^0$ where $R^0$ is alkyl of 1 to 24 carbon atoms such as n- octyl, n-dodecyl, n-octadecyl and n-tetracosanyl, preferably $R^3$ is alkylthioethyl of 5 to 21 atoms in the chain where $R^0$ is 2 to 18 carbon atoms.

Where $n$ is 2, $R^3$ is also alkylene of 2 to 12 carbon atoms such as ethylene, tertramethylene, 2,2-di-methylpropylene, hexamethylene, octamethylene or dodecamethylene. Preferably $R^3$ is alkylene of 2 to 8 carbon atoms and most preferably 2 to 6 carbon atoms.

$R^3$ can also be thiobis-alkylene of 5 to 9 atoms in the chain such as thiodiethylene and thiodibutylene, preferably $R^3$ is thiodiethylene.

$R^3$ is cycloalkylene of 5 to 8 carbon atoms such as 1,3-cyclopentanediyl, 1,4-cyclohexanediyl and 2,2,4,4-tetramethyl-1,3-cyclobutanediyl. Preferably $R^3$ is 2,2,4,4-tetramethyl-1,3-cyclobutanediyl.

$R^3$ can also be alkylene of 7 to 10 carbon atoms containing a cycloalkane group in the chain such as 1,4-cyclohexanedimethylene and 1,5-cyclooctanedimethylene. Preferably $R^3$ is 1,4-cyclohexanedimethylene.

$R^3$ is also alkyleneoxyalkylene of 5 to 9 atoms in the chain such as oxydiethylene, oxydibutylene and oxydi(1,2-propylene). Preferably $R^3$ is oxydiethylene.

$R^3$ can also be polyoxyalkylene of 8 to 101 atoms having the general structure $-R^\infty(OR^\infty)_h-$ where $R^\infty$ is a straight or branched lower alkylene of 2 to 4 carbon atoms and $h$ is 2 to 33. $R^\infty$ is ethylene, 1,2-propylene, 1,2-butylene and tetramethylene. Preferably $R^3$ is polyoxyalkylene of 8 to 11 atoms where $R^\infty$ is ethylene and $h$ is 2 to 3. Most preferably $R^3$ is polyoxyethylene of 8 atoms in the chain.

Where $n$ is 3 to 6, $R^3$ is a polyvalent cyclic or acrylic hydrocarbon radical of 3 to 10 carbon atoms such as 1,2,3-propanetriyl, neopentanetriyl, neopentanetetrayl, 2,2-dimethyl-1,2,2-butanetriyl, 2,2-diemthyl-1,2,2-pentanetriyl, 1,2,3,4,5,6-cyclohexanehexayl or 1,2,3,4,5,6-hexanehexayl. Preferably $R^3$ is a polyvalent acyclic hydrocarbon radical of 3 to 7 carbon atoms and most preferably of 5 to 7 carbon atoms.

$R^4$ is hydrogen or lower alkyl of 1 to 8 carbon atoms such as methyl, ethyl, butyl, and octyl. Preferably $R^4$ is hydrogen or lower alkyl of 1 to 4 carbon atoms. Most preferably $R^4$ is hydrogen or methyl. $R^4$ is also cycloalkyl of 5 to 6 carbon atoms, preferably cyclohexyl.

Where $m$ is 2, $R^4$ can be the group

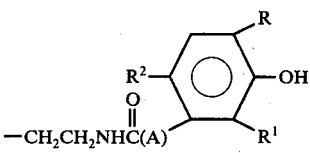

when diethylene triamine or triethylene tetramine are used in the preparation of the amides of formula II.

When $m$ is 2 and $R^4$ and $R^5$ together form a piperazinyl ring with the nitrogen atoms of formula II, the amide stabilizers of this invention have the structure

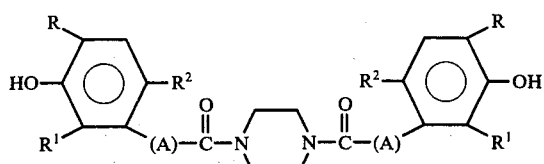

$R^5$ can be alkyl of 1 to 24 carbon atoms such as methyl, octyl, n-dodecyl or n-tetracosanyl, preferably of 1 to 18 carbon atoms such as n-octadecyl.

$R^5$ is also phenyl or phenyl substituted with alkyl groups, said alkyl groups having 1 to 18 carbon atoms. The substituents may be methyl, isopropyl, tert-butyl and tert-octyl with substitution preferably in the ortho or para positions of the phenyl ring.

Where $m$ is 2, $R^5$ is alkylene or 2 to 18 carbon atoms such as ethylene, octamethylene and octadecamethylene. Preferably $R^5$ is alkylene of 2 to 12 carbon atoms such as ethylene, hexamethylene and dodecamethylene.

$R^5$ can also be alkyleneoxyalkylene of 5 to 9 atoms in the chain such as oxydiethylene, oxydibutylene and oxydi(1,2-propylene). Preferably $R^5$ is oxydiethylene.

Where $m$ is 3 to 4, $R^5$ is a polyvalent cyclic or acyclic hydrocarbon radical of 3 to 8 carbon atoms such as neopentanetetrayl, neopentanetriyl, 1,2,3-propanetriyl and 1,4-dimethylcyclohexan-1,1,4,4-tetrayl.

A is a straight or branched lower alkylene of 1 to 8 carbon atoms such as methylene, ethylene, trimethylene, 1,2-propylene and 1,2-octylene. A is also a 1,1-alkylidene group of 2 to 8 carbon atoms such as ethylidene, 1,1-n-butylidene and 1,1-n-octylidene. Preferably A is a striaght chain alkylene of 1 to 3 carbon atoms, that is, methylene, ethylene and trimethylene, and most preferably is methylene or ethylene.

The integer $m$ is 1 to 4 and preferably is 1 to 2.
The integer $n$ is 1 to 6 and preferably is 1 to 4.

The ester stabilizers of this invention are prepared via usual esterification procedures from a suitable alcohol or polyol, alkyl substituted phenol, or polyhydric phenol and an acid of formula III

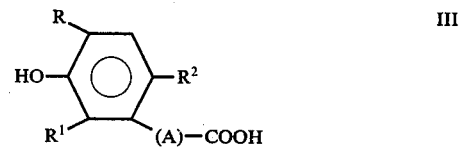

or an acid halide or acid anhydride thereof. Aryl esters are especially conveniently made by reaction of the acid halide with hydroxyaryl compounds, for example, phenol, alkyl substituted phenols, polyhydric phenols, naphthols, etc.

The higher alkyl esters are prepared from the lower alkyl ester, especially the methyl ester of the above represented compounds, by transesterification with a higher alkanol or polyol.

A further embodiment of this invention are nitriles of the formula IV

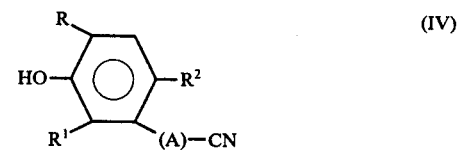

Compounds of formula IV are stabilizers and are also intermediates for conversion to carboxylic acids of formula III. For example, carboxylic acids of formula III, where A is methylene or 1,1-alkylidene of 2 to 8 carbon atoms, are readily prepared from IV by hydrolysis. Where A is ethylene, the carboxylic acid of formula III is also prepared as outlined in the following equation;

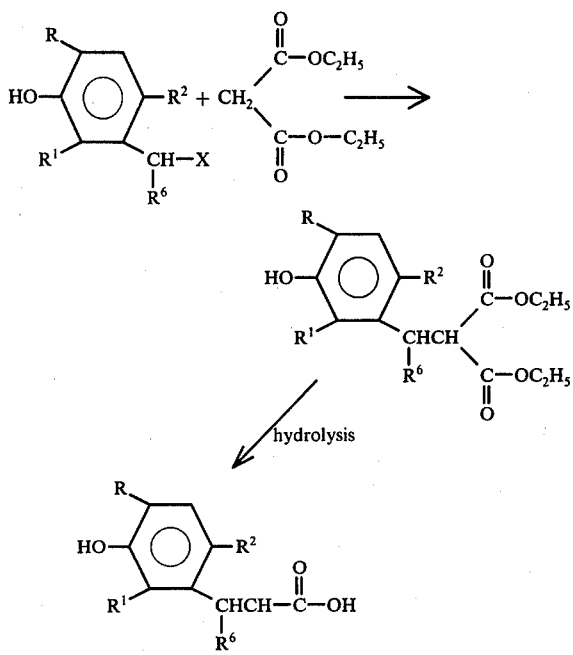

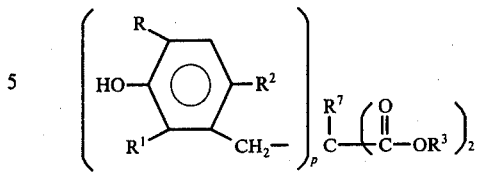

where X is chlorine or bromine and $R^6$ is hydrogen or lower alkyl of 1 to 7 carbon atoms. 2,4,6-Trialkyl-3-halomethylphenols, such as 6-tert.-butyl-3-chloromethyl-2,4-dimethylphenol, are prepared by reaction of hydrogen halide and formaldehyde and the appropriate starting phenol following procedures described by Wegler et al (Makr. Chem. 9,22 (1952).

Where A is a substituted methylene, the carboxylic acid of formula III is prepared conveniently by the halomethylation reaction using a 2,4,6-trialkylphenol, hydrogen chloride or bromide and the appropriate aldehyde $R^6$CHO. The starting phenols employed in the preparation of the stabilizers of this invention are commercially available or prepared by known methods. Of particular interest are phenols which have branched alkyls or cycloalkyls in an ortho position to the OH of the phenyl ring. Thus, for example the preparation of the following is described in the following references, all of them being prepared by alkylation or cycloalkylation reactions.

6-tert-butyl-2,4-dimethylphenol and 6-cyclohexyl-2,4-dimethylphenol — G. Parc, Revue Inst. Franc. Vol XV, page 689 (1960)

6-(2-methylcyclohexyl)-2,4-dimethylphenol — Lambert and Williams, U.S. Pat. No. 2,839,493 (June 17, 1958)

6-sec. octyl-2,4-dimethylphenol — S. A. Dmitrier et al Khim. Technol. Topl. Masel 12 (3),12–16 (1967)

6-(1,1,2-trimethylpropyl)-2,4-diemthylphenol — Gura et al, Zh. Organ. Khim. 1 (6),1055-7 (1965)

6-isopropyl-2,4-dimethylphenol — Demerseman et al, Bull, Soc. Chim. France 1962, 1700-5.

The amides of this invention are prepared by known procedures for example, by reacting the carboxylic acid of formula II or an acid chloride or anhydride thereof with the appropriate amine. The higher alkanamides can also be prepared from the lower alkyl esters of the acid of formula III by known amidation procedures.

A further embodiment of this invention are trialkyl substituted hydroxphenylalkylene malonate esters of the formula V $$\left( \begin{array}{c} R \\ HO-\bigcirc-R^2 \\ R^1 \quad CH_2- \end{array} \right)_p \begin{array}{c} R^7 \\ | \\ C \end{array} \left( \begin{array}{c} O \\ \| \\ C-OR^3 \end{array} \right)_2 \quad (V)$$

wherein

R, $R^1$, $R^2$ and $R^3$ are as previously defined, n is 1 or 2, with the additional proviso that $R^7$ is hydrogen when p is 1 and $R^7$ is nil when p is 2.

The compounds of this invention are stabilizers of organic material normally subject to thermal and oxidative deterioration. Materials which are thus stabilized include synthetic organic polymeric substances such as vinyl resins formed from the polymerization of vinyl halides or from the copolymerization of vinyl halides with unsaturated polymerizable compounds, e.g., vinyl esters, α,β-unsaturated ketones, α,β-unsaturated aldehydes and unsaturated hydrocarbons such as butadienes and styrene; poly-α-olefins such as polyethylene, polypropylene, polybutylene including copolymers of α-olefins such as ethylene/propylene copolymer dienes such as polybutadiene, polyisoprene, and the like, including copolymers with other monomers; polyurethanes and polyamides such as polyhexamethylene adipamide and polycaprolactam; polyesters such as polyethylene terephthalates; polycarbonates; polyacetals such as polyethylene terephthalate polyacetal; polystyrene, polyethylene oxide; polyphenylene oxide and copolymers; and copolymers such as those of high impact polystyrene and those formed by the copolymerization of acrylonitrile, butadiene and/or styrene; natural and synthetic rubbers such as ethylene/propylene/diene copolymer (EPDM) and chlorinated rubber.

Other materials which can be stabilized by the compounds of the present invention include lubricating oil of the aliphatic ester type, i.e., di(2-ethylene azelate and other synthetic ester lubricants, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., β-methoxyethylene glycol, methoxytriethylene glycol, triethylene glycol, octaethylene glycol, dibutylene glycol, dipropylene glycol and the like.

The substrates of particular importance are olefin polymers such as polyethylene and polypropylene. Polypropylene is especially well stabilized with the compounds of this invention.

In general, the stabilizers of this invention are employed from about 0.01 to about 5% by weight of the stabilized composition, although this will vary with the particular substrate and application. An advantageous range is from about 0.05 to about 2% and especially from 0.1 to about 1%.

For addition to polymeric substrates, the stabilizers can be blended before polymerization or after polymerization, during the usual processing operations, for example, by hot-milling, the compositions then being extruded, pressed, or the like into films, fibers, filaments, hollow spheres and the like. The heat stabilizing properties of these compounds advantageously stabilize the polymer against degradation during such processing at the high temperature generally encountered. The stabilizers can also be dissolved in suitable solvents and sprayed on the surface of films, fabrics, filaments or the like to provide effective stabilization.

These compounds can also be used in combination with other additives such as sulfur-containing esters, e.g., distearyl β-thiodipropionate (DSTDP), dilauryl β-thiodipropionate (DLTDP), in an amount of from 0.01 to 2% by weight of the organic material, and the like, pourpoint depressants, corrosion and rust inhibitors, dispersing agents, emulsifiers, antifoaming agents, carbon black, accelerators and other chemicals used in rubber compounding, plasticizers, color stabilizers, di- and tri-alkyl- and alkylphenylphosphites, heat stabilizers, untraviolet light stabilizers, antiozonants, surface active agents, fillers, dyes, pigments, metal chelating agents, dyesites and the like. Often combinations such as these, particularly the sulfur-containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

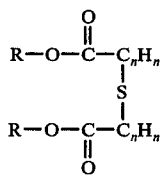

wherein R is an alkyl group having from 6 to 24 carbon atoms; and $n$ is an integer from 1 to 6. Especially useful compounds of this type are dilauryl β-thiodipropionate and distearyl β-thiodipropionate. The above co-stabilizers are used in the amount of from 0.01 to 2% by weight of the organic material, and preferably from 0.1 to 1%.

The stabilizers of this invention are particularly useful in protecting polymer compositions subjected to high temperature processing as well as end uses involving elevated temperatures. Polymer compositions containing these stabilizers are resistant to discoloration.

In addition to the above noted additives that can be employed in combination with the compounds of this invention, it is often especially advantageous to employ also light stabilizers. The light stabilizers are used in the amount of from 0.01 to 5% by weight of the organic material, and preferably from 0.1 to 1%. Illustrative examples of light stabilizers are listed below.

UV-absorbers and light protection agents 2-(2'-hydroxyphenyl)-benztriazoles, such as, for example, the 5'-methyl-, 3',5'-di-tert.-butyl-,5'-tert.-butyl-, 5'-(1,1,3,3-trimethyl-butyl)-, 5-chloro-3', 5'-di-tert.-butyl-, 5-chloro-3'-tert.-butyl-5'methyl-, 3'-sec.-butyl-5'-tert.-butyl-, 3'-{α-methylbenzyl}-5'-methyl-, 3'-{α-methylbenzyl}-5'-methyl-5-chloro-, 4'-hydroxy-, 4'-methoxy-, 4'-octoxy-, 3',5'-di-tert.-amyl-, 3'-methyl-5'-carbomethoxyethyl- or 5-chloro-3',5'-di-tert.-amyl-derivative.

2,4-bis-(2'-hydroxyphenyl)-6-alkyl-s-triazines, such as, for example, the 6-ethyl-, 6-undecyl- or 6-heptadecyl-derivative.

2-hydroxy-benzophenones, such as, for example, the 4-hydroxy-, 4-methoxy-, 4-octoxy-, 4-decyloxy-, 4-dodecyloxy-, 4-benzyloxy-, 4,2',4'-trihydroxy- or 2'-hydroxy-4,4'-dimethoxy-derivative.

1,3-bis-(2'-hydroxy-benzoyl)-benzenes, such as for example. 1,3-bis-(2'-hydroxy-4'-hexyloxy-benzoyl)-benzene, 1,3-bis-(2'-hydroxy-4'-octoxy-benzoyl)-benzene and 1,3-bis-(2'-hydroxy-4'-dodecyloxy-benzoyl)-benzene.

Esters of optionally substituted benzoic acids, such as, for example, phenyl salicylate, octylphenyl salicylate, di-benzoylresorcinol, bis-(4-tert.-butylbenzoyl)-resorcinol, benzoyl-resorcinol, 3,5-di-tert.-butyl-4-hydroxybenzoic acid 2,4-di-tert.-butyl-phenyl ester, octadecyl ester or 2-methyl-4,6-di-tert.-butylphenyl ester.

Acrylates, such as, for example, α-cyano-β,β-diphenyl acrylic acid ethyl ester or isooctyl ester, α-carbomethoxy-cinnamic acid methyl ester, α-cyano-β-methyl-p-methoxy-cinnamic acid methyl ester or butyl ester and N-(β-carbomethoxy-vinyl)-2-methyl-indoline.

Nickel compounds, such as, for example, nickel complexes of 2,2'-thio-bis-4-(1,1,3,3-tetramethylbutyl)-phenyl, such as the 1:1 and 1:2 complex, optionally with other ligands such as n-butylamine, triethanolamine or N-cyclohexyl-diethanolamine; nickel complexes of bis-{2-hydroxy-4-(1,1,3,3-tetramethylbutyl)-phenyl}sulphone, such as the 2:1 complex, optionally with other ligands such as 2-ethyl-caproic acid; nickel dibutyldithiocarbamate, nickel salts of 4-hydroxy-3,5-di-tert.-butyl-benzyl-phosphonic acid monoalkyl esters, such as the methyl, ethyl or butyl ester, the nickel complex of (2-hydroxy-4-methyl-phenyl)-undecyl-ketonoxime and nickel 3,5-di-tert.-butyl-4-hydroxy-benzoate.

Oxalic acid diamides, such as, for example, 4,4'-dioctyloxyoxanilide, 2,2'-dioctyloxy-5,5'-di-tert.-butyl-oxanilide, 2,2'-di-dodecyloxy-5,5'-di-tert.-butyl oxanilide, 2-ethoxy-5-tertiarybutyl-2'-ethyl-oxanilide, 2-ethoxy-2'-ethyl-oxanilide, N,N'-bis-(3-dimethylamino-propyl) oxalamide, mixtures of o- and p-methoxy and o- and p-ethoxy-di-substituted oxanilides and mixtures of 2-ethoxy-5-tert.-butyl-2'-ethyl-oxanilide with 2-ethoxy-2'-ethyl-5,4'-di-tert.-butyl-oxanilide.

Sterically hindered amines, such as, for example 4-benzoyloxy-2,2,6,6-tetramethylpiperidine, 4-stearoyloxy-2,2,6,6-tetramethylpiperidine, bis-(2,2,6,6-tetramethylpiperidyl)-sebacate and 3-n-octyl-7,7,9,9-tetramethyl-1,3-triaza-spiro[4,5]decane-2,4-dione.

For exemplification purposes only listed below are compounds of this invention which are useful as stabilizers as discussed above.

4-t-butyl-2,6-dimethyl-3-hydroxyphenyl acetic acid
3-(2,4,6-trimethyl-3-hydroxyphenyl)propionic acid
4-(4-t-octyl-2,6-diethyl-3-hydroxyphenyl)-butyric acid
8-(4-cyclohexyl-2,6-dimethyl-3-hydroxyphenyl)-octanoic acid
n-octadecyl 4-t-butyl-2,6-dimethyl-3-hydroxyphenylacetate
2-(n-octylthio)ethyl 4-t-butyl-2,6-dimethyl-3-hydroxyphenylacetate
1,6-hexamethylene bis-(4-t-butyl-2,6-dimethyl-3-hydroxyphenylacetate)
methyl 4-t-butyl-2,6-dimethyl-3-hydroxyphenylacetate
neopentanetriyl tris-(4-t-butyl-2,6-dimethyl-3-hydroxyphenylacetate)
2-(n-octadecylthio)ethyl 4-tert.-butyl-2,6-dimethyl-3-hydroxyphenylacetate neopentanetetrayl tetrakis-(4-t-butyl-2,6-dimethyl-3-hydroxyphenylacetate)

3,6-dioxa-1,8-octamethylene bis-(4-t-octyl-2,6-dimethyl-3-hydroxyphenylacetate)

thiodiethylene bis-(4-t-butyl-2,6-dimethyl-3-hydroxyphenylacetate)

n-octadecyl 3-(4-t-butyl-2,6-dimethyl-3-hydroxyphenyl)propionate n-dodecyl 3-(4-t-butyl-2,6-dimethyl-3-hydroxyphenyl)propionate methyl 3-(4-t-butyl-2,6-dimethyl-3-hydroxyphenyl)propionate phenyl 4-t-butyl-2,6-dimethyl-3-hydroxy-phenylacetate p-t-octylphenyl 4-t-butyl-2,6-dimethyl-3-hydroxyphenylacetate neopentyl 4-t-butyl-2,6-dimethyl-3-hydroxyphenylacetate n-octyl 2,4,6-trimethyl-3-hydroxyphenylacetate 2-(n-octadecylthio)ethyl 3-(4-isopropyl-2,6-dimethyl-3-hydroxyphenyl)propionate 2-ethylhexyl 3-(4-t-butyl-2,6-dimethyl-3-hydroxyphenyl)propionate 2,2-dimethylpropylene bis-[3-(4-cyclohexyl-2,6-dimethyl-3-hydroxyphenyl)propionate]

1,2-propylene bis-[3-(4-t-butyl-2,6-dimethyl-3-hydroxyphenyl)propionate]

2,2-dimethylpropylene bis-[4-(4-t-butyl-2,6-diethyl-3-hydroxyphenyl)butyrate]

1,8-octamethylene bis-[3-(2,6-di-butyl-4-methyl-3-hydroxyphenyl)propionate]

1-6-hexamethylene bis-[3-(4-t-butyl-2,6-dimethyl-3-hydroxyphenyl)propionate]

1,12-dodecamethylene bis-[3-(4-cyclopentyl-2,6-dimethyl-3-hydroxyphenyl)propionate]

2,2-dimethyl-1,2,2-butanetriyl tris-[3-(4-t-butyl-2,6-dimethyl-3-hydroxyphenyl)propionate]

1,2,3-propanetriyl tris-[3-(4-t-butyl-2,6-dimethyl-3-hydroxyphenyl)propionate]

2,2-dimethyl-1,2,2-pentanetriyl tris(4-t-butyl-2,6-dimethyl-3-hydroxyphenylacetate)

neopentanetetrayl tetrakis(4-t-butyl-2,6-dimethyl-3-hydroxyphenylacetate)

1,2,3-butanetriyl tris-[4-(2,4,6-triisopropyl-3-hydroxyphenyl)butyrate]

o-methylphenyl 3-(4-t-octyl-2,6-dimethyl-3-hydroxyphenyl)propionate 1,2,3,4,5,6-cyclohexanehexayl hexakis-(4-tert-butyl-2,6-dimethyl-3-hydroxyphenylacetate)

n-tetracosanyl 3-(4-tert-octyl-2,6-dimethyl-3-hydroxyphenyl)propionate cyclohexyl 4-tert-butyl-2,6-dimethyl-3-hydroxyphenylacetate n-octadecyl (4-tert-butyl-2,6-dimethyl-3-hydroxyphenyl)-α-methylacetate n-octyl (4-tert-butyl-2,6-dimethyl-3-hydroxyphenyl)-α-n-heptylacetate neopentanetetrayl tetrakis-[3-(4-t-octyl-2,6-dimethyl-3-hydroxyphenyl)propionate]

3-(4-tert-butyl-2,6-dimethyl-3-hydroxyphenyl)-propionamide 4-tert-butyl-2,6-dimethyl-3-hydroxyphenylacetamide N-methyl-N-n-tetracosanyl-(4-tert-octyl-2,6-dimethyl-3-hydroxyphenyl)acetamide N-n-octyl-N-phenyl-3-(4-tert-octyl-2,6-dimethyl-3-hydroxyphenyl)propionamide N-cyclohexyl-3-(4-tert-butyl-2,6-dimethyl-3-hydroxy-phenyl)propionamide N,N-di-n-butyl-(4-cyclohexyl-2,6-dimethyl-3-hydroxyphenyl)acetamide N,N',N'',N'''-1,4-dimethylcyclohexan-1,1,4,4-tetrayl tetrakis [3-(4-tert-butyl-2,6-dimethyl-3-hydroxyphenyl)propionamide]

N-o-tolyl-N-methyl-(4-tert-octyl-2,6-dimethyl-3-hydroxyphenyl)acetamide

The following examples are illustrative of the invention, but are not meant to limit the scope of same. In said examples, parts are by weight unless otherwise indicated and the relationship between parts by weight and parts by volume is as that between grams and cubic centimeters. The temperatures are in degrees centigrade.

EXAMPLE 1

6-tert.-Butyl-3-chloromethyl-2,4-dimethylphenol

The compound of this example was made by a procedure described by Wegler, et al (Makr. Chem. 9,22(1952)). After crystallization from petroleum ether, the product was obtained as white crystals melting at 45° to 47° C.

EXAMPLE 2

6-tert.-Octyl-3-chloromethyl-2,4-dimethylphenol

The compound of this example was made by a procedure analogous to the compound of Example 1. After recrystallization from petroleum ether, the desired compound was isolated as white crystals melting at 80° to 83° C.

EXAMPLE 3

4-tert.-Butyl-2,6-dimethyl-3-hydroxyphenylacetonitrile

To 41 grams of potassium cyanide dispersed in 300 ml of N,N-dimethylformamide, was slowly added a solution of 97.2 grams of the compound of Example 1, the reaction temperature rising from 25° to 35° C. The reaction mixture was then heated at 70° to 75° for 7½ hours. Since a sample analyzed after 7 hours reaction time indicated that some unreacted starting 6-tert.-butyl-3-chloromethyl-2,4-dimethylphenol remained unreacted, an additional 13.7 grams of potassium cyanide was added and the reaction mixture heated for an additional 2 hours at 60° to 65° C. The reaction mixture was poured on crushed ice, and water added to make the total volume 1.8 liters. The mixture was stirred until the ice melted, the aqueous solid dispersion was filtered by suction, and the filtercake washed well with water. The filtercake was taken up in a toluene-benzene mixture, the resulting solution being successively washed with water, 6N aqueous hydrochloric acid and dried over anhydrous sodium sulfate. After removal of the drying agent by filtration and treating the clear filtrate with activated charcoal, the solvent was evaporated at reduced pressures. The resulting residue was allowed to crystallize from toluene yielding white crystals melting at 134° to 139°.

EXAMPLE 4

4-tert.-Octyl-2,6-dimethyl-3-hydroxyphenylacetonitrile

This compound was made substantially in the same manner as described in Example 3 yielding white crystals melting at 109° to 111° after crystallization from n-hexane.

EXAMPLE 5

4-tert.-Butyl-2,6-dimethyl-3-hydroxyphenylacetic acid 65.1 grams of the compound of Example 3 was added with stirring to a solution of 36 grams of sodium hydroxide in 40 ml of ethylene glycol and 66 ml of water. The reaction mixture became homogeneous at about 116° to 117° and was heated at this temperature for two hours. The reaction mixture was cooled by the addition of chopped ice and cold water to the reaction mixture to make a total volume of one liter. After clarifying the reaction mixture by filtration, the filtrate was made acid with concentrated aqueous hydrochloric acid, yielding a white precipitate, which was filtered, washed with cold water and dried. The product was then treated with rapid stirring at 50° C with about 800 ml of 6% sodium bicarbonate solution until carbon dioxide evolution stopped. The turbid solution was filtered free of a white solid-by-product. (A). The clarified filtrate was made acid with concentrated hydrochloric acid while cooling, and the resulting white precipitate filtered. After washing with hot water and drying the product was obtained as a white powder melting at 161° to 165°.

After recrystallizations from toluene and aqueous methanol the melting point was 165° to 167°.

EXAMPLE 6

4-tert.-Butyl-2,6-dimethyl-3-hydroxyphenylacetamide

By-product (A) isolated in Example 5 was crystallized from benzene containing a little ethanol yielding the white crystals melting at 194° to 196° C. Carbon, hydrogen, nitrogen microanalysis, infrared spectra and NMR all confirm that this compound is 4-tert.-butyl-2,6-dimethyl-3-hydroxyphenylacetamide.

EXAMPLE 7

4-tert.-Octyl-2,6-dimethyl-3-hydroxyphenylacetic acid

This compound was made in a similar manner to the method disclosed in Example 5 by hydrolyzing 4-tert.-octyl-2,6-dimethyl-3-hydroxyphenylacetonitrile with sodium hydroxide in aqueous ethylene glycol. After crystallization from toluene 4-tert.-octyl-2,6-dimethyl-3-hydroxyphenylacetic acid melted at 157° to 159° C.

EXAMPLE 8

4-tert.-Octyl-2,6-dimethyl-3-hydroxyphenylacetamide

As in Example 5, a by-product insoluble in aqueous sodium hydroxide formed in Example 7. After crystallization from toluene this by-product was obtained in pure form and melted at 179° to 181°. (Compound 10)

EXAMPLE 9 n-Octadecyl 4-tert.-butyl-2,6-dimethyl-3-hydroxyphenylacetate 10.68 grams of the compound of Example 5, 11.4 grams of n-octadecanol and 0.8 grams of p-toluene sulfonic acid monohydrate were dispersed in 150 ml of toluene and heated at reflux for seven hours during which the water collected by azeotropic distillation was almost equal to the theory. The reaction mixture was successively washed with water, aqueous saturated sodium bicarbonate solution, and then with water once again until the wash water was neutral. After drying over anhydrous sodium sulfate and filtering free of the drying agent, the clear filtrate was evaporated at reduced pressures to yield the desired product as residue. After successive crystallizations from acetonitrile and n-heptane, the desired compound was isolated as white crystals melting at 57° to 59° C (Compound 1).

Other 4-tert.-butyl-2,6-dimethyl-3-hydroxyphenylacetates made in a similar manner as Example 9 are shown in Table I.

TABLE I

Other 4-tert.-butyl-2,6-dimethyl-3-hydroxyphenylacetates $$\left(HO-\underset{CH_3}{\overset{\times}{\underset{}{\bigcirc}}}-\underset{CH_2-C-O}{\overset{CH_3}{\underset{\parallel}{}}}\right)_n R^3$$

| Compound No. | n | $R^3$ | M.P. ° C. |
|---|---|---|---|
| 2 | 1 | n-$C_{18}H_{37}$—S—$CH_2CH_2$— | 53–56 |
| 3 | 2 | —$(CH_2)_6$— | 133–136 |

EXAMPLE 10

Methyl 4-tert.-butyl-2,6-dimethyl-3-hydroxyphenylacetate 43.4 grams of 4-tert.-butyl-2,6-dimethyl-3-hydroxyphenylacetic acid (Example 5) was added to 200 ml of methanol which had previously been saturated with hydrogen chloride gas at 15° C yielding a turbid solution which became clear at 30° C. The reaction solution was then heated at reflux for 2½ hours. The reaction mixture was diluted with about 600 ml of an ice-water mixture and stirred until all the ice had melted, yielding a dispersion of the solid methyl ester desired which was filtered and washed with water. The filtercake was dissolved in benzene and successively washed with warm saturated aqueous sodium bicarbonate and water until the wash water was neutral. After drying over anhydrous sodium sulfate and filtering free of drying agent and removing the solvent at reduced pressures, the residue was obtained as a solid melting at 90° to 93°. Recrystallization from methanol containing a little water yielded white crystals melting at 90° to 93° (Compound 4).

EXAMPLE 11

Neopentanetriyl tris-(4-tert.-butyl-2,6-dimethyl-3-hydroxyphenylacetate)

16.5 grams of the compound of Example 10, 2.4 grams of 1,1,1-trimethylolethane and 9.6 milligrams of lithium hydride were heated together with stirring in a dry nitrogen atmosphere at 140° to 145° for 2¾ hours and at 150° to 155° for 1¾ hours at one atmosphere. The reaction melt was then heated with stirring at 155° for 6 hours at 20 mm Hg. pressure. After addition of about 0.1 to 0.2 grams of glacial acetic acid to neutralize the lithium catalyst, the glassy reaction mixture was dissolved in 200 ml of warm benzene containing about 25 ml of chloroform, clarified by filtration and the resulting clear solution successively washed with water, aqueous 3N hydrochloric acid, water, 2N aqueous sodium hydroxide and finally with water again until wash water was neutral. After drying over anhydrous sodium sulfate and filtering free of drying agent, the clear filtrate was concentrated at reduced pressures to yield a glassy residue. Successive crystallizations from carbon tetrachloride and acetonitrile yielded white crystals melting at 165° to 167° (Compound 5).

2,2-Dimethylpropylene bis(4-tert.-butyl-2,6-dimethyl-3-hydroxyphenylacetate) is prepared in a similar manner as the compound of Example 11 by substituting 2,2-dimethyl-1,3-propanediol for 1,1,1-trimethylolethane.

EXAMPLE 12

Neopentanetetrayl tetrakis-(4-tert.-butyl-2,6-dimethyl-3-hydroxyphenylacetate 15.5 grams of the compound of Example 10, 1.90 grams of pentaerythritol, 6.7 milligrams of lithium hydride and 1.3 ml of dimethyl sulfoxide were melted and heated together in a dry nitrogen atmosphere at 135° to 140° for 2 hours, 140° to 145° for 1 hour and 145° to 150° for another 2 hours. The reaction mixture was then heated at 20 mm Hg. nitrogen pressure at 150° to 165° for 16 hours. The vacuum was then released with nitrogen and an additional 6 milligrams of lithium hydride was introduced and heating continued for an additional 24 hours at 20 mm Hg. nitrogen pressure at 160° to 165°. The glassy reaction product was dissolved in 100 ml of warm benzene containing 0.5 ml of glacial acetic acid and the solution washed successively with water, 3N aqueous hydrochloric acid, 2N aqueous sodium hydroxide and finally with water until the wash water was neutral. After drying over anhydrous sodium sulfate and removing the drying agent by filtration, the clear filtrate was freed of solvent by distillation at reduced pressures yielding a brown glassy residue. The glassy residue was crystallized twice from carbon tetrachloride. The desired product was isolated in pure form by elution column chromatography using silica gel G (Grace) using a solvent mixture of 50 parts by volume of benzene and 50 parts by volume of hexane as eluant, the purified product being found after the benzene-hexane eluant was evaporated to dryness at reduced pressures. After crystallization from carbon tetrachloride, the desired product was obtained as white crystals melting at 153° to 155° (Compound 6).

Thiodiethylene bis-(4-tert.-butyl-2,6-dimethyl-3-hydroxyphenylacetate) is made by an analogous rocedure as the product of Example 12 by substituting thiodiglycol for pentaerythritol.

EXAMPLE 13

3,6-Dioxa-1,8-octamethylene bis-(4-tert.-octyl-2,6-dimethyl-3-hydroxyphenylacetate)

9.7 grams of 4-tert.-octyl-2,6-dimethyl-4-hydroxyphenylacetic acid, 2,2 grams of triethyleneglycol and 0.57 grams of p-toluenesulfonic acid monohydrate were dispersed together in 150 ml of toluene and heated at reflux for 15 hours, the water of reaction being removed by azeotropic distillation. After washing the toluene reaction mixture successively with water, 2N aqueous sodium hydroxide and again with water and removing the solvent by distillation in vacuum, the residue was successively crystallized from acetonitrile and nitromethane yielding white crystals melting at 114° to 120° (Compound 7).

EXAMPLE 14

Diethyl 4-tert.-butyl-2,6-dimethyl-3-hydroxybenzylmalonate 1.15 grams of small pieces of sodium and 1.8 grams of diethyl malonate in 80 ml of dry heptane were heated together at 55° to 60° for 1 hour and then at reflux for 2½ hours forming the sodium salt of diethyl malonate as a white dispersion in n-heptane. To the above white dispersion was added dropwise over a period of 20 minutes at 25° to 26° 11.45 grams of 6-tert.-butyl-3-chloromethyl-2,4-dimethylphenol dissolved in 25 ml of dry heptane, the reaction mixture being heated at reflux for 8½ hours. After addition of about 100 ml of ether to the reaction mixture and washing the resulting turbid solution successively with water, 6N aqueous hydrochloric acid and again with water to pH5, the clear solution was dried over anhydrous sulfate, and the solvent was removed by distillation in vacuum. The residue was crystallized from petroleum ether yielding the product as white crystals melting at 56° to 59°. (Compound 11)

EXAMPLE 15

Di-n-octadecyl 4-tert.-butyl-2,6-dimethyl-3-hydroxybenzylmalonate 6.3 grams of the compound of Example 14, 9.8 grams of n-octadecanol and 0.890 grams of dibutyltin oxide were heated together as a melt at 130° to 140° for 3 hours, 140° to 150° for 1 hour in a rapid stream of nitrogen to remove the ethanol of reaction. Finally the reaction mixture was heated at 145° to 150° at 20 to 25 mm Hg. pressure for 2 hours. The solidified melt was dissolved in 100 ml of toluene and successively washed with water, aqueous 6N hydrochloric acid, water and saturated sodium bicarbonate solution, the toluene solution being dried over anhydrous sodium sulfate. After removal of the toluene by distillation at reduced pressures and purification by elution chomatography over activated alumina (Woelm, Activity II), the residue was crystallized from hexane yielding white crystals melting at 72° to 74°. (Compound 12)

EXAMPLE 16

4-tert.-Butyl-2,6-dimethyl-3-hydroxybenzylmalonic acid 35 grams of the compound of Example 14 was dissolved in 125 ml of methanol together with 12.3 grams of sodium hydroxide dissolved in 50 ml of water and heated at reflux for 6 hours. After removal of most of the methanol by distillation at reduced pressure, 300 ml of water was added and stirred to yield a turbid solution which was clarified by filtration. The clear filtrate was extracted with ether, and the ether extract washed with water and dried over anhydrous sodium sulfate. After removal of the ether by distillation at reduced pressure, the glassy residue was crystallized from 1,2-dichloroethane yielding white crystals melting at 174°.

EXAMPLE 17

3-(4-tert.-Butyl-2,6-dimethyl-3-hydroxyphenyl)propionic acid 17.9 grams of the compound of Example 16 was stirred together with white oil at 165° to 180° for two hours until little $CO_2$ evolution could be detected. The reaction mixture was cooled to 50° and stirred thoroughly together with 5.2 grams of sodium bicarbonate dissolved in 100 ml of water until no foaming took place and all solids had dissolved. The reaction mixture was diluted with 50 ml of n-hexane and the upper organic phase separated from the lower aqueous phase. The organic phase was washed with water, the wash water being combined with the aqueous phase. The combined aqueous phase was then washed with n-hexane, clarified by filtration through filtercel, and added dropwise to about 150 ml of cold 6N aqueous hydrochloric acid so that a granular off-white precipitate was obtained. The product was used as such after drying in the vacuum oven at 60° and 3mm Hg. overnight.

EXAMPLE 18

Methyl 3-(4-tert.-butyl-2,6-dimethyl-3-hydroxyphenyl)propionate 13.6 grams of the product of Example 17 was dissolved in 200 ml of methanol saturated with anhydrous hydrogen chloride gas at 15° C, heated at reflux (60° to 71°) for 3 hours, and then concentrated to one-third volume by distilling off solvent at reduced pressure. After pouring the concentrate on an icewater mixture while stirring, the resulting crystalline precipitate was taken up in toluene, the toluene solution being successively washed with water, aqeuous 2N sodium hydroxide, saturated sodium chloride solution and water until the pH of the wash water was neutral. After drying over anhydrous sodium sulfate and removal of the solvent by distillation at reduced pressure, the residue was ground to a powder and freed of colored impurities by trituration with petroleum ether. Crystallization from n-heptane yielded the product as white crystals melting at 108° to 110° (Compound 8).

EXAMPLE 19 n-Octadecyl 3-(4-tert.-butyl-2,6-dimethyl-3-hydroxyphenyl)propionate 6.4 grams of the compound of Example 18, 6.24 grams of n-octadecanol and 9.6 milligrams of lithium hydride were melted together under nitrogen at 110° C and then heated with stirring at 125° to 135° for 2 hours, at 140° to 155° for 1½ hours and at 155° for 45 minutes at 20 mm Hg. pressure. The reaction mixture was dissolved in 200 ml of toluene containing 1 ml of acetic acid, the toluene solution being then successively washed with aqueous 6N hydrochloric acid, water, aqueous 2N sodium hydroxide, saturated sodium chloride and water until pH5. After drying the toluene solution over sodium sulfate and removing the toluene by distillation at reduced pressure, the residue was crystallized from methanol yielding white crystals melting at 49° to 51° (Compound 9).

n-Dodecyl 3-(4-tert.-butyl-2,6-dimethyl-3-hydroxyphenyl)propionate is obtained by using the procedure of Example 19 by substituting n-dodecanol for n-octadecanol.

EXAMPLE 20

4-tert.-Butyl-2,6-dimethyl-3-hydroxyphenylacetyl chloride 47.2 g (0.20 moles) of 4-t-butyl-2,6-dimethyl-3-hydroxyphenyl acetic acid, and 0.4 ml of dry N,N-dimethylformamide are dispersed in 325 ml of dry benzene. To this slurry was added dropwise with stirring under a nitrogen atmosphere 28.5 g (17.5 ml, 0.24 moles) of thionyl chloride at ambient temperature. The reaction mixture was allowed to stir for 16 hours, then evaporated under reduced pressure, yielding an orange-colored solid, which proved by analysis to be the desired acid chloride. The residue was dissolved in 500 ml of benzene, analyzed for chloride ion and used for subsequent reactions in solution.

EXAMPLE 21 phenyl 4-tert.-butyl-2,6-dimethyl-3-hydroxyphenylacetate

Triethylamine is added dropwise to an equimolar mixture of phenol and the compound of Example 20 in benzene at room temperature and allowed to react at ambient temperature. After filtration of the triethylamine hydrochloride the product is recovered by removing the solvent by distillation.

p-tert.-Octylphenyl 4-tert.-butyl-2,6-dimethyl-3-hydroxyphenylacetate is made in analogous manner by substituting p-tert.-octylphenol for phenol in the above procedure.

EXAMPLE 22

N-Methyl-N-n-octadecyl-4-tert.-butyl-2,6-dimethyl-3-hydroxyphenylacetamide

A solution of 10.19 gms of 4-tert.-butyl-2,6-dimethyl-3-hydroxyphenylacetyl chloride in 100 ml of benzene was added dropwise at 10° to 12° with stirring over a 40 minute period to a solution in 200 ml of dry benzene of 22.64 (0.08 moles) of N-methyl-N-n-octadecylamine and stirring overnight at room temperature. After filtering free of the precipitated solid, the filtrate was evaporated under reduced pressure and the residue recrystallized from heptane, yielding white crystals, m.p. 115° to 116.5° of the desired material (Compound 13).

EXAMPLE 23

N,N-Dimethyl 4-tert.-butyl-2,6-dimethyl-3-hydroxyphenylacetamide

This compound was prepared by a similar procedure to that of Example 22 by substituting anhydrous dimethylamine for N-methyl-N-octadecylamine. After crystallization from benzene the product was obtained as white crystals melting at 191° to 194° (Compound 14).

EXAMPLE 24

N,N'-Bis(4-t-butyl-2,6-dimethyl-3-hydroxyphenylacetyl)piperazine

To a solution of 3.45 g (0.04 moles) of piperazine and 8.5 g (0.084 moles) of triethylamine in 100 ml of dry benzene was added dropwise with stirring at 10° to 12° over a period of 40 minutes a solution of 20.38 g (0.08 moles) of 4-t-butyl-2,6-dimethyl-3-hydroxyphenylacetyl chloride in 200 ml of benzene. The reaction mixture was allowed to stir overnight at room temperature then was heated at reflux for two hours. The reaction mixture was then cooled, filtered with suction and the collected solids washed well with water. The water insoluble material was recrystallized from a solvent mixture of chloroform/N,N-dimethylformamide yielding white crystals, m.p. 305° to 310° after drying, of the desired material (Compound 15).

EXAMPLE 25

N-n-Octadecyl-4-t-butyl-2,6-dimethyl-3-hydroxyphenylacetamide 21 g (0.084 moles) of methyl 4-t-butyl-2,6-dimethyl-3-hydroxyphenylacetate and 22.6 g (0.084 moles) of n-octadecylamine were heated together over a period of 3 hours under a nitrogen atmosphere to 185° to 195° C. The reaction mixture was then held at this temperature until the expected amount of methanol was obtained by distillation. The reaction product was washed with heptane, dissolved in benzene, and filtered through a layer of silica gel. After evaporation of the benzene solution at reduced pressure, the product was recrystallized from heptane, yielding the desired material as white crystals, m.p. 88° to 94° C (Compound 16).

EXAMPLE 26

N-n-Octyl-4-tert.-butyl-2,6-dimethyl-3-hydroxyphenylacetamide

This product was made by an essentially similar procedure as described in Example 25 by substituting n-octylamine for n-octadecylamine. The product is obtained as white crystals melting at 101° to 104° after crystallization from n-heptane (Compound 17).

EXAMPLE 27

N,N'-Bis-(4-tert.-butyl-2,6-dimethyl-3-hydroxyphenylacetyl)hexamethylenediamine This compound was made by an analogous procedure to Example 25 by substituting 0.5 molar equivalent of hexamethylenediamine for n-octadecylamine. After crystallization from a solvent mixture of acetone/cyclohexane the product is obtained as white crystals melting at 202° to 204° (Compound 18).

Unstabilized polypropylene powder (Hercules Profax 6501) was thoroughly blended with 0.2% by weight of the indicated stabilizer compound. Also prepared were samples of polypropylene containing 0.1% by weight of the same stabilizer and 0.3% by weight of DSTDP (distearyl β-thiodipropionate). The blended materials were then milled on a two-roll mill at 182° C for 10 minutes, after which time the stabilized polypropylene was sheeted from the mill and allowed to cool.

The milled polypropylene sheets were then cut into pieces and pressed for 7 minutes on a hydraulic press at 218° C, 19.25 Kg/cm² pressure. The resulting plaques of 0.635 mm thickness were tested for resistance to accelerated aging in a forced draft oven at 150° C.

When the plaques showed the first signs of decomposition (e.g., cracking or brown edges) they were considered to have failed. The results are shown in Table II, Table III and Table IV.

TABLE II
OVEN AGING OF ALKYLSUBSTITUTED HYDROXYPHENYLALKANOATES IN POLYPROPYLENE

| Ex. No. | Percent Stabilizer | Hours to Failure |
|---|---|---|
| 27 | No Stabilizer | 3 |
| 28 | 0.2% Compound 4 | < 20 |
| 29 | 0.1% Compound 4 + 0.3% DSTDP | 160 |
| 30 | 0.2% Compound 1 | 75 |
| 31 | 0.1% Compound 1 + 0.3% DSTDP | 635 |
| 32 | 0.2% Compound 2 | 810 |
| 33 | 0.1% Compound 2 + 0.3% DSTDP | 1440 |
| 34 | 0.2% Compound 3 | 245 |
| 35 | 0.1% Compound 3 + 0.3% DSTDP | 1320 |
| 36 | 0.2% Compound 5 | 360 |
| 37 | 0.1% Compound 5 + 0.3% DSTDP | 1680 |
| 38 | 0.2% Compound 6 | 340 |
| 39 | 0.1% Compound 6 + 0.3% DSTDP | 1620 |
| 40 | 0.2% Compound 7 | 260 |
| 41 | 0.1% Compound 7 + 0.3% DSTDP | 1140 |
| 42 | 0.2% Compound 8 | < 20 |
| 43 | 0.1% Compound 8 + 0.3% DSTDP | 135 |
| 44 | 0.2% Compound 9 | 130 |
| 45 | 0.1% Compound 9 + 0.3% DSTDP | 725 |

Correspondingly good stabilization is achieved when the stabilizer concentration is varied from 0.01 to 2%.

The stabilizers are particularly effective in the presence of a thio ester co-stabilizer such as DSTDP.

TABLE III
OVEN AGING OF ALKYLSUBSTITUTED HYDROXYBENZYLMALONATE STABILIZERS IN POLYPROPYLENE

| Ex. No. | Percent Stabilizer | Hours to Failure |
|---|---|---|
| 46 | No Stabilizer | 3 |
| 47 | 0.2% Compound 11 | < 20 |
| 48 | 0.1% Compound 11 + 0.3% DSTDP | 270 |
| 49 | 0.2% Compound 12 | 200 |
| 50 | 0.1% Compound 12 + 0.3% DSTDP | 2075 |

Correspondingly good stabilization is achieved when the stabilizer concentration is varied from 0.01 to 2%.

TABLE IV
OVEN AGING OF AMIDE STABILIZER IN POLYPROPYLENE

| Ex. No. | Percent Stabilizer | Hours to Failure |
|---|---|---|
| 51 | No Stabilizer | 3 |
| 52 | 0.2% Compound 10 | < 20 |
| 53 | 0.1% Compound 10 + 0.3% DSTDP | 165 |
| 54 | 0.2% Compound 13 | 275 |
| 55 | 0.1% Compound 13 + 0.3 DSTDP | 980 |
| 56 | 0.2% Compound 14 | < 20 |
| 57 | 0.1% Compound 14 + 0.3 DSTDP | 145 |
| 58 | 0.2% Compound 15 | 120 |
| 59 | 0.1% Compound 15 + 0.3 DSTDP | 1165 |
| 60 | 0.2% Compound 16 | 130 |
| 61 | 0.1% Compound 16 + 0.3 DSTDP | 535 |
| 62 | 0.2% Compound 17 | < 20 |
| 63 | 0.1% Compound 17 + 0.3 DSTDP | 260 |
| 64 | 0.2% Compound 18 | 310 |
| 65 | 0.1% Compound 18 + 0.3 DSTDP | 625 |

Correspondingly good stabilization is achieved when the stabilizer concentration is varied from 0.01 to 2%.

The stabilizers are particularly effective in the presence of a thio ester co-stabilizer such as DSTDP.

EXAMPLE 66

Pellets (500 g) of unstabilized nylon-6,6 (Zytel 101, DuPont) are placed in a Kitchen Aid Mixer. With mixing a solution of 0.5% (based on the weight of nylon) of methyl 3-(2,4,6-trimethyl-3-hydroxyphenyl)propionate in 20 ml of methylene chloride is added slowly. Sodium hypophosphite (0.5 gm 0.1%) is dissolved in 20 ml of water and added slowly with mixing to the nylon pellets after the antioxidant solution has been added and most of the methylene chloride has evaporated. The stabilized pellets are dried at 80° C at <1 mm Hg for 4 hours.

The polyamide formulation is extruded at 315.6° C through at 0.625 cm die into a rod which is water cooled and chopped into pellets. A 1.905 cm Brabender extruder, equipped with a nylon screw, is used. The pellets are dried at 80° C at <1 mm for 4 hours.

The dried pellets are compression molded into 0.127 mm thick film by pressing at 290° C for 4 minutes at 57.75 Kg/cm². The films are oven aged at 150° C in a forced draft oven and samples are removed periodically. The specific viscosity of the samples are determined using a 1% formic acid solution at 25° C. The sample stabilized with the above noted stabilizer required longer aging time to reduce its viscosity by one-half than the unstabilized sample.

EXAMPLE 67

Unstabilized high impact polystyrene resin is dry blended with 0.01% by weight of the resin of methyl 8-(4-cyclohexyl-2,6-dimethyl-3-hydroxyphenyl)octanoate. The resin is then extrusion compounded on a 2.54 cm 24/1=L/D extruder, melt temperature 260° C and then pressed for 7 minutes at a temperature of 163° C and a pressure of 140 Kg/cm² into a sheet of uniform thickness of 2.54 mm. The sheets are then cut into plaques of 5.08 cm × 5.08 cm. The plaques are then oven aged at 80° C and color measurements made periodically using a Hunter Color Difference Meter Model D25. The polystyrene samples stabilized with the above stabilizer develops the undesirable yellow discoloration substantially later than the time that such discoloration occurred in the unstabilized samples.

EXAMPLE 68

Unstabilized linear polyethylene (HiFax 4401) is solvent blended in methylene chloride with 0.5% by weight of the substrate of n-octadecyl 3-(4-t-butyl-2,6-di-methyl-3-hydroxyphenyl)propionate and then vacuum dried. The resin is then extruded at 232.2° C using a 1.905 cm extruder having a 24:1 L/D ratio. The melt flow rate of a sample of the resin is determined after each extrusion according to ASTM test D-1238. Polyethylene stabilized with above compound is found to undergo less change in the melt flow rate than the unstabilized polyethylene.

EXAMPLE 69

A quantity of SBR emulsion containing 100 g of rubber (500 ml of a 20% SBR emulsion obtained commercially from Texas U.S. as Synpol 1500) previously stored under nitrogen, is placed in a beaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% NaCl solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1 mm) at 40° to 45° C.

The dried rubber (25 g) is heated under nitrogen at 125° C in a Brabender mixer and to this is added with mixing 0.1% 2-(n-octadecylthio)ethyl 3(4-isopropyl-2,6-dimethyl-3-hydroxyphenyl)propionate.

Portion of the rubber are oven aged at 100° C. At various intervals gel content is determined on the rubber. The rubber stabilized with the above compound shows much less gel formation than the unstabilized sample.

EXAMPLE 70

To 50 g of polyacetal resin containing 0.1% of an acid scavenger, dicyandiamide, is added 0.2% by weight of 2-ethylhexyl 3-(4-t-butyl-2,6-dimethyl-3-hydroxyphenyl)propionate and milled for 7 minutes at 200° C in a Brabender Plasti-recorder. The milled formulation is subsequently pressed into a 1.016 mm sheet at 215° C at 24.5 Kg/cm² for 90 seconds then cooled quickly in a cold press at 24.5 Kg/cm². The stabilized sheets are then remolded for 2 minutes at contact pressure and for 3 minutes at 21 Kg/cm² at 215° C to give plaques 3.81 cm × 5.715 cm × 3.175 mm.

The plaques are aged in the oven at 60° C and the weight loss of the specimen is determined periodically until a 4% weight loss is reached. The stabilized sample takes a much longer time to reach this 4% weight loss than does the unstabilized sample.

EXAMPLE 71

Unstabilized, thoroughly dried polyethylene terephthalate chips are dry blended with 1.0% of 1,2-propylene bis[3-(4-cyclohexyl-2,6-dimethyl-3-hydroxyphenyl)propionate]. 60/10 denier multifilament is melt spun at a melt temperature of 290° C. and cold oriented 3 to 1. The oriented fibers are wound into skeins and oven aged at 140° C. The stabilized material exhibits greater retention of tensile strength after 24 hours than the unstabilized material.

EXAMPLE 72

A stabilized high temperature lubricating oil is prepared by incorporating 2% by weight of 2,2-dimethyl-1,2,2-butanetriyl tris-[3-(4-t-butyl-2,6-dimethyl-3-hydroxyphenyl)propionate] to the lubricant which comprises diisoamyl adipate. The stabilized composition is compared with the unstabilized lubricant by heating at 175° C in the presence of air and metallic catalysts according to the test method described in Military Specification Mil-I-7808c. After 72 hours, the blank containing no stabilizer contains more sludge and has a greater viscosity than the stabilized lubricant.

What is claimed is:

1. A compound having the formula

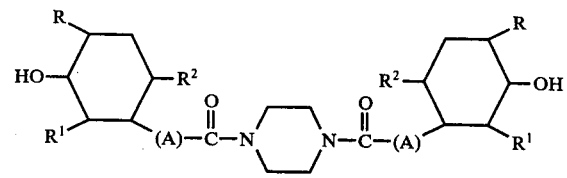

wherein
R is a branched alkyl of 3 to 8 carbon atoms,
R¹ and R² are alkyl of 1 to 3 carbon atoms, and
A is a straight chain alkylene of 1 to 3 carbon atoms.

2. A compound of claim 1 wherein R is a branched chain alkyl and R¹ and R² are straight chain alkyl.

3. A compound of claim 1 wherein R is tert-alkyl and R¹ and R² are methyl.

4. The compound of claim 1, N,N'-bis(4-tert.butyl-2,6-dimethyl-3-hydroxyphenylacetyl)piperazine.

* * * * *